(12) United States Patent
Simpson et al.

(10) Patent No.: US 10,603,078 B2
(45) Date of Patent: Mar. 31, 2020

(54) SURGICAL INSTRUMENT AND METHOD

(71) Applicant: Warsaw Orthopedic, Inc, Warsaw, IN (US)

(72) Inventors: Joshua W. Simpson, Collierville, TN (US); Rodney R. Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 62 days.

(21) Appl. No.: 15/334,942

(22) Filed: Oct. 26, 2016

(65) Prior Publication Data

US 2018/0110544 A1  Apr. 26, 2018

(51) Int. Cl.
*A61B 17/70* (2006.01)
*A61B 17/88* (2006.01)

(52) U.S. Cl.
CPC ...... *A61B 17/7022* (2013.01); *A61B 17/7002* (2013.01); *A61B 17/7053* (2013.01); *A61B 17/7083* (2013.01); *A61B 17/8869* (2013.01)

(58) Field of Classification Search
CPC ..... A61B 17/82; A61B 17/823; A61B 17/842; A61B 17/844; A61B 17/8645; A61B 17/8861; A61B 17/8869; A61B 2017/0408; A61B 2017/042; A61B 2017/0425; A61B 2017/0427; A61B 2017/0446; A61B 2017/0448; A61B 2017/0454; A61B 2017/0487; A61B 2017/868

See application file for complete search history.

(56) References Cited

U.S. PATENT DOCUMENTS

| 5,312,410 | A | * | 5/1994 | Miller | A61B 17/8861 606/103 |
| 5,395,374 | A | * | 3/1995 | Miller | A61B 17/82 606/103 |
| 5,540,698 | A | * | 7/1996 | Preissman | A61B 17/82 606/103 |
| 6,689,140 | B2 | * | 2/2004 | Cohen | A61B 17/8861 606/103 |
| 8,162,946 | B2 | | 4/2012 | Baccelli et al. | |
| 2002/0071753 | A1 | * | 6/2002 | Bjorklund | B60P 7/135 414/555 |

(Continued)

FOREIGN PATENT DOCUMENTS

| WO | 2005079686 A1 | 9/2005 |
| WO | 2016137879 A1 | 9/2016 |

OTHER PUBLICATIONS

International Search Report, Korean Intellectual Property Office, PCT/US2017/057789, dated Feb. 7, 2018.

*Primary Examiner* — Lynnsy M Summitt

(57) ABSTRACT

A surgical instrument comprises a first member defining a cavity and including a locking surface disposed with the cavity. The locking surface is engageable with a longitudinal member to fix a tether with the first member. A second member includes an inner surface that defines a longitudinal passageway configured for disposal of a surgical driver engageable with a spinal construct. The second member further includes at least one mating element being engageable with the spinal construct. An actuator is connected with the members and is configured to incrementally tension the tether. Systems, implants and methods are disclosed.

20 Claims, 15 Drawing Sheets

(56) References Cited

U.S. PATENT DOCUMENTS

| | | | |
|---|---|---|---|
| 2002/0133159 A1* | 9/2002 | Jackson | A61B 17/7032 606/916 |
| 2004/0138666 A1* | 7/2004 | Molz, IV | A61B 17/88 606/74 |
| 2010/0106194 A1* | 4/2010 | Bonutti | A61B 17/0218 606/279 |
| 2013/0072983 A1* | 3/2013 | Lindquist | A61B 17/7049 606/278 |
| 2013/0261680 A1* | 10/2013 | Baccelli | A61B 17/7053 606/86 A |
| 2013/0268011 A1 | 10/2013 | Rezach et al. | |
| 2014/0039567 A1* | 2/2014 | Hoefer | A61B 17/708 606/86 A |
| 2014/0094850 A1* | 4/2014 | Clement | A61B 17/7001 606/263 |
| 2014/0257397 A1* | 9/2014 | Akbarnia | A61B 17/8869 606/263 |
| 2014/0257401 A1* | 9/2014 | George | A61B 17/7041 606/278 |
| 2016/0038182 A1 | 2/2016 | Gorek et al. | |
| 2016/0038194 A1* | 2/2016 | Belliard | A61B 17/7053 606/263 |
| 2016/0262806 A1* | 9/2016 | Hsu | A61B 17/7076 |
| 2016/0374736 A1* | 12/2016 | Hsu | A61B 17/7076 606/86 A |
| 2017/0354445 A1* | 12/2017 | Deneuvillers | A61B 17/7083 |

* cited by examiner

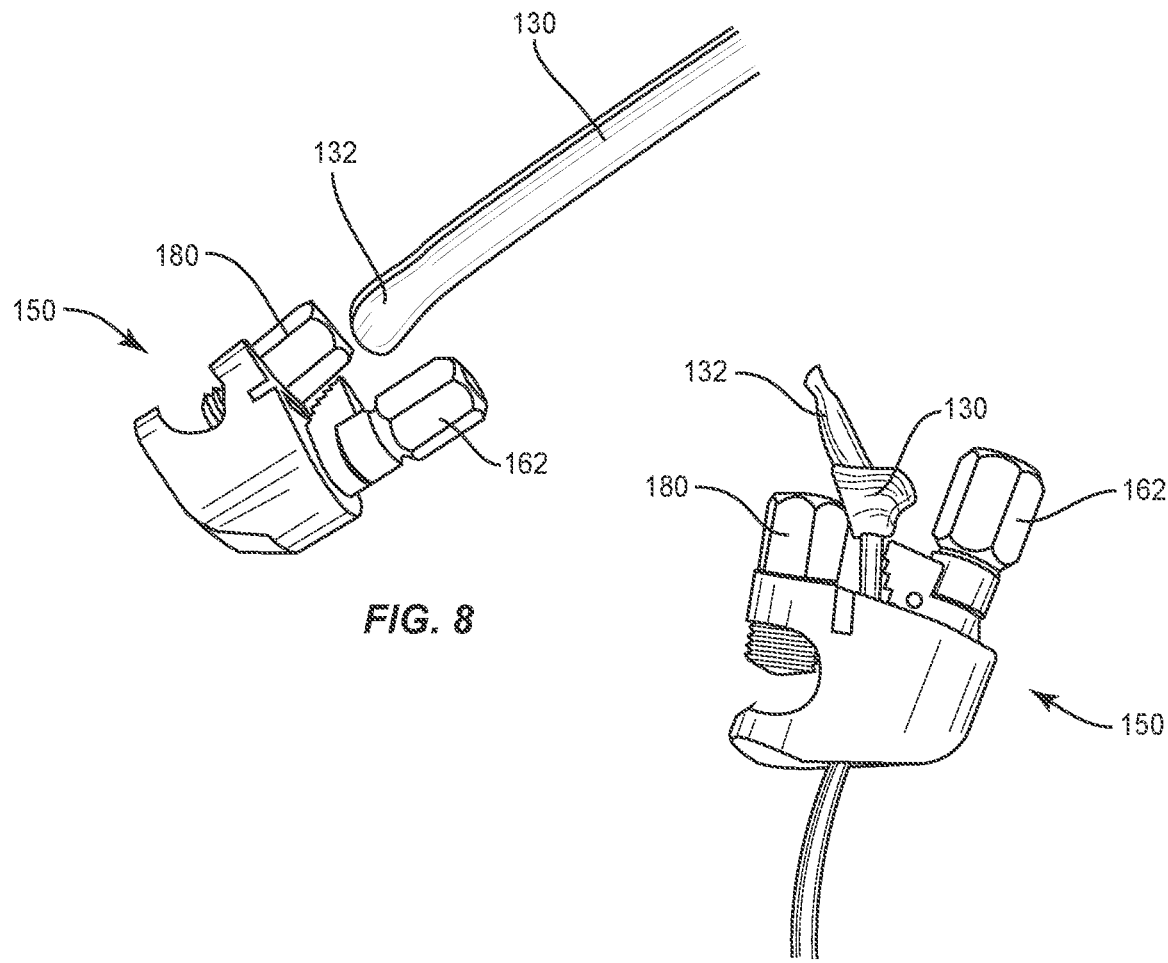
FIG. 8
FIG. 9
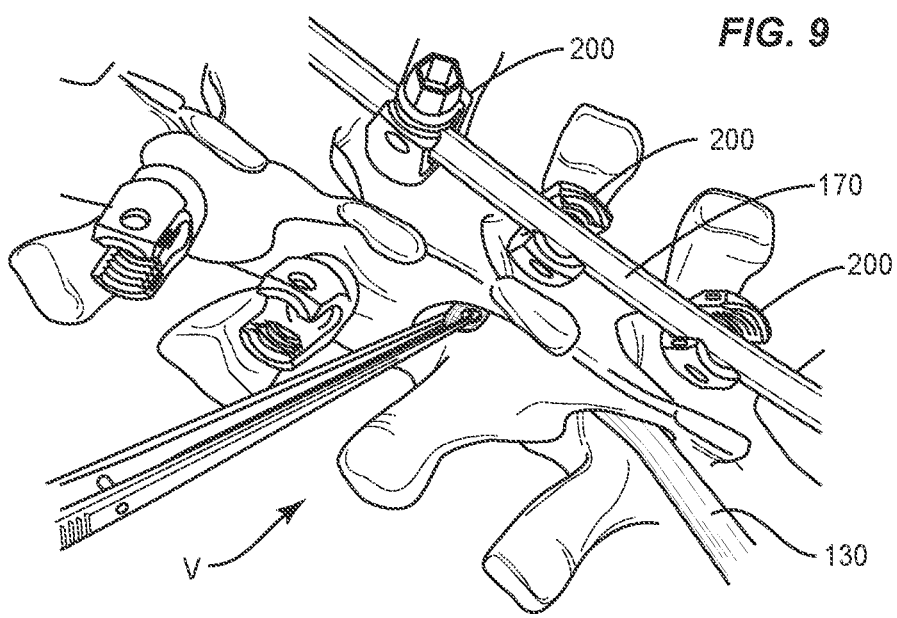
FIG. 10

SURGICAL INSTRUMENT AND METHOD

TECHNICAL FIELD

The present disclosure generally relates to medical devices for the treatment of spinal disorders, and more particularly to a surgical instrument and method for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as tethers, bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the implants for attachment to the exterior of one or more vertebral members. This disclosure describes an improvement over these prior technologies.

SUMMARY

In one embodiment, a surgical instrument is provided. The surgical instrument comprises a first member defining a cavity and includes a locking surface disposed with the cavity. The locking surface is engageable with a tether to fix the tether with the first member. A second member includes an inner surface that defines a longitudinal passageway configured for disposal of a surgical driver engageable with a spinal construct. The second member further includes at least one mating element that is engageable with the spinal construct. An actuator is connected with the members and is configured to incrementally tension the tether. In some embodiments, systems, implants and methods are disclosed.

In one embodiment, a surgical system is provided. The surgical system comprises a tether. A connector is configured for disposal of the tether. A spinal rod is configured for disposal with the connector. A coupling member is engageable with the spinal rod and the connector. A surgical instrument includes a first member defining a cavity and includes a locking surface disposed with the cavity. The locking surface is engageable with the tether to fix the tether with the first member. The surgical instrument further includes a second member including an inner surface that defines a longitudinal passageway. At least one mating element is engageable with the connector and an actuator is connected with the members to incrementally tension the tether. A surgical driver is disposable with the longitudinal passageway and engageable with the coupling member.

In one embodiment, a method for treating a spine is provided. The method comprises the steps of: delivering a spinal construct to a surgical site including vertebrae, the spinal construct including a connector configured for disposal of a tether and a spinal rod, the spinal construct further including a coupling member engageable with the spinal rod and the connector; connecting the tether with the vertebrae; mating a surgical instrument with the connector, the surgical instrument including a first member having a locking surface being engageable with the tether and a second member that defines a longitudinal passageway; tensioning the tether with the surgical instrument; and guiding a surgical driver through the longitudinal passageway for connection with the coupling member.

BRIEF DESCRIPTION OF THE DRAWINGS

The present disclosure will become more readily apparent from the specific description accompanied by the following drawings, in which:

FIG. 8 is a perspective view of one embodiment of components of a surgical system in accordance with the principles of the present disclosure;

FIG. 9 is a perspective view of one embodiment of components of a surgical system in accordance with the principles of the present disclosure;

FIG. 10 is a perspective view of one embodiment of components of a surgical system in accordance with the principles of the present disclosure disposed with vertebrae;

DETAILED DESCRIPTION

Figure 1:
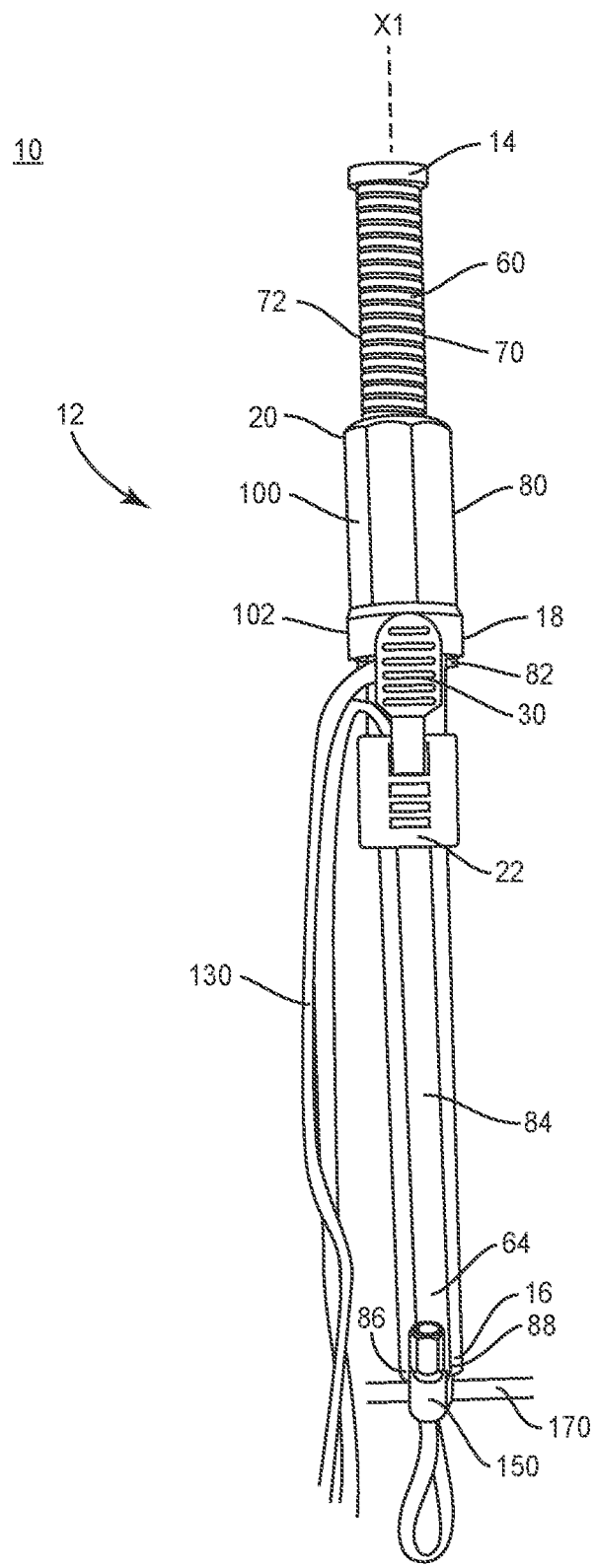
FIG. 1 is a side view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the surgical system includes a surgical instrument that comprises a tether tensioner. In some embodiments, the surgical system includes a surgical instrument that comprises a sub-laminar tether tensioner. In some embodiments, the tether tensioner includes a counter-torque, which can be employed for final tightening of one or more components of a spinal construct connected with vertebrae. In some embodiments, the surgical system provides a tensioner for providing tension to a tether portion of a connector. In some embodiments, the surgical system includes a surgical instrument that provides, for example, loading one or more implants of a spinal construct, for example, a connector to a spinal rod and into a body. In some embodiments, the surgical system is employed with a method that includes the step of affixing a connector to a spinal rod and providing counter-torque to tighten a set screw, and tensioning a tether. In some embodiments, the surgical instrument includes a ratcheting mechanism to tension a tether. In some embodiments, the surgical instrument includes a threaded mechanism to tension a tether.

In some embodiments, the surgical system is employed with a method that includes the step of reducing a spinal rod to a spine and applying tension to a sub-laminar tether. In some embodiments, the method includes the step employing a surgical tensioner instrument to reduce the spinal rod and apply tension to the sub-laminar tether. In some embodiments, the surgical instrument includes a ratcheting tensioner that uses teeth and a pawl to move a carriage away from a spinal construct while pulling a tether. In some embodiments, the surgical instrument includes a threaded tensioner. In some embodiments, the surgical instrument includes a threaded tensioner that moves a threaded carriage away from a spinal construct while drawing a tether.

In some embodiments, the surgical instrument includes a ratcheting tensioner that includes a ratcheting mechanism. In some embodiments, the ratcheting tensioner includes a catch that resists and/or prevents a carriage from translating downward while a pawl resets. In some embodiments, the catch cannot be released while a cam lever arm of the ratcheting mechanism is engaged, which resists and/or prevents accidental release of the carriage while a tether is under tension.

In some embodiments, the ratcheting tensioner includes a lever that drives the pawl downward, forcing the carriage upward. In some embodiments, a single actuation or engagement, for example, squeezing of the lever produces translation of the carriage. In some embodiments, a single actuation of the lever produces 1.5 millimeters (mm) of translation of the carriage. In some embodiments, the ratcheting tensioner includes a cam lock to attach the carriage with a tether. In some embodiments, the ratcheting tensioner includes a safety latch that resists and/or prevents disengagement of the tether from the carriage. In some embodiments, the ratcheting tensioner includes a carriage that defines a tether path.

In some embodiments, the surgical instrument includes one or more locks to fix a spinal rod and/or a connector with the tensioner. In some embodiments, the surgical instrument includes one or more tabs to lock the surgical instrument to a connector. In some embodiments, the surgical instrument includes an outer sleeve that resists and/or prevents the tabs from releasing the connector. In some embodiments, the surgical instrument includes an outer sleeve that locks a spinal rod in position.

In some embodiments, the surgical system includes a surgical instrument configured to apply a tension to a sub-laminar tether. In some embodiments, the surgical system includes a tensioner configured to apply a tension to a tether and/or a spinal construct. In some embodiments, the tensioner is configured for attachment with a spinal construct, such as, for example, a connector. In some embodiments, the tensioner is configured for attachment with the connector via mating surfaces. In some embodiments, the mating surfaces include one or more slots. In some embodiments, the tensioner includes a mating element for engagement with slots disposed with the connector. In some embodiments, the tensioner comprises an implant holder.

In some embodiments, the surgical system includes a tether configured for engagement with the connector. In some embodiments, the surgical instrument includes a threaded shaft to facilitate translation of a carriage in a direction away from the connector by rotation along a threaded shaft. In some embodiments, the surgical instrument includes a knob to actuate translation and apply a tension to the tether.

In some embodiments, the surgical system includes one or more implants, such as, for example, a sub-laminar tether and a connector. In some embodiments, the surgical system includes one or more surgical instruments, such as, for example, a tensioner, a socket driver and a counter-torque handle. In some embodiments, the tether includes a tip having a 90 mm length to facilitate passage under a lamina. In some embodiments, the tether includes a 750 mm length to facilitate wrapping of the tether about the tensioner.

In some embodiments, the surgical system includes a connector having slots configured to facilitate connection of the connector with a surgical instrument. In some embodiments, the slots provide visual indicia of the connector for mating and/or docking with a surgical instrument. In some embodiments, the slots provide access to a top surface of the connector by a surgical instrument to control axial translation and facilitate engagement of the surgical instrument therewith. In some embodiments, the tether is connected with the connector by a screw similar to a screw utilized for connection of the connector with a spinal rod. In some embodiments, the surgical system includes a t25 torx screw for connection of the connector with a spinal rod and a t25 torx screw for connecting the tether with the connector.

In some embodiments, the surgical system includes a tensioner connected with a spinal rod such that the tensioner engages along a surface of the spinal rod and/or has a run on the spinal rod of 25 mm. In some embodiments, the surgical system includes a tensioner having a medial-lateral width of 25 mm. In some embodiments, the surgical system includes a tensioner having a member including a triple lead thread. In some embodiments, the triple lead thread is configured to provide for increase in advancement time of a carriage with a decrease in mechanical advantage. In some embodiments, the carriage is configured to translate 9.5 mm per rotation and includes 75 mm of thread length. In some embodiments, indicia, such as, for example, hash marks are provided on the member as a reference guide. In some embodiments, the carriage includes a cam lock having a decreased length and a larger actuation surface for manipulation.

In some embodiments, the surgical system includes a tensioner having a projection configured to straighten tension on the tether. In some embodiments, the projection is configured to resist and/or prevent the tether from contacting sharp surfaces. In some embodiments, the surgical system includes a socket driver. In some embodiments, the socket driver is configured to provide additional torque to facilitate tensioning. In some embodiments, the socket driver is configured to provide segmental tensioning if multiple tensioners are utilized. In some embodiments, the surgical system includes a counter-torque handle engageable with the tensioner. In some embodiments, the counter-torque handle is configured to facilitate fracturing break off portions of set screws.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-5, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g.; Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 comprises a surgical instrument, such as, for example, a tensioner 12. Tensioner 12 extends between an end 14 and an end 16. Tensioner 12 defines a longitudinal axis X1. In some embodiments, tensioner 12 may comprise overall and/or cross-section configurations, such as, for example, cylindrical, round, oval, rectangular, polygonal, irregular, tapered, offset, staggered, uniform and non-uniform. In some embodiments, one or more of the surfaces of tensioner 12 may have alternate surface configurations, such as, for example, rough, threaded for connection with surgical instruments, arcuate, undulating, porous, semi-porous, dimpled, polished and/or textured.

Tensioner 12 includes a member, such as, for example, a carriage 18. Carriage 18 extends between an end 20 and an end 22. In some embodiments, carriage 18 may have various configurations, for example, circular, cylindrical, square, oval, rectangular, polygonal, irregular, tapered, offset, staggered and uniform. Carriage 18 includes an outer surface 24. In some embodiments, outer surface 24 may have alternate surface configurations, such as, for example, smooth, rough, threaded for connection with surgical instruments, arcuate, undulating, porous, semi-porous, dimpled, polished and/or textured.

Figure 2:
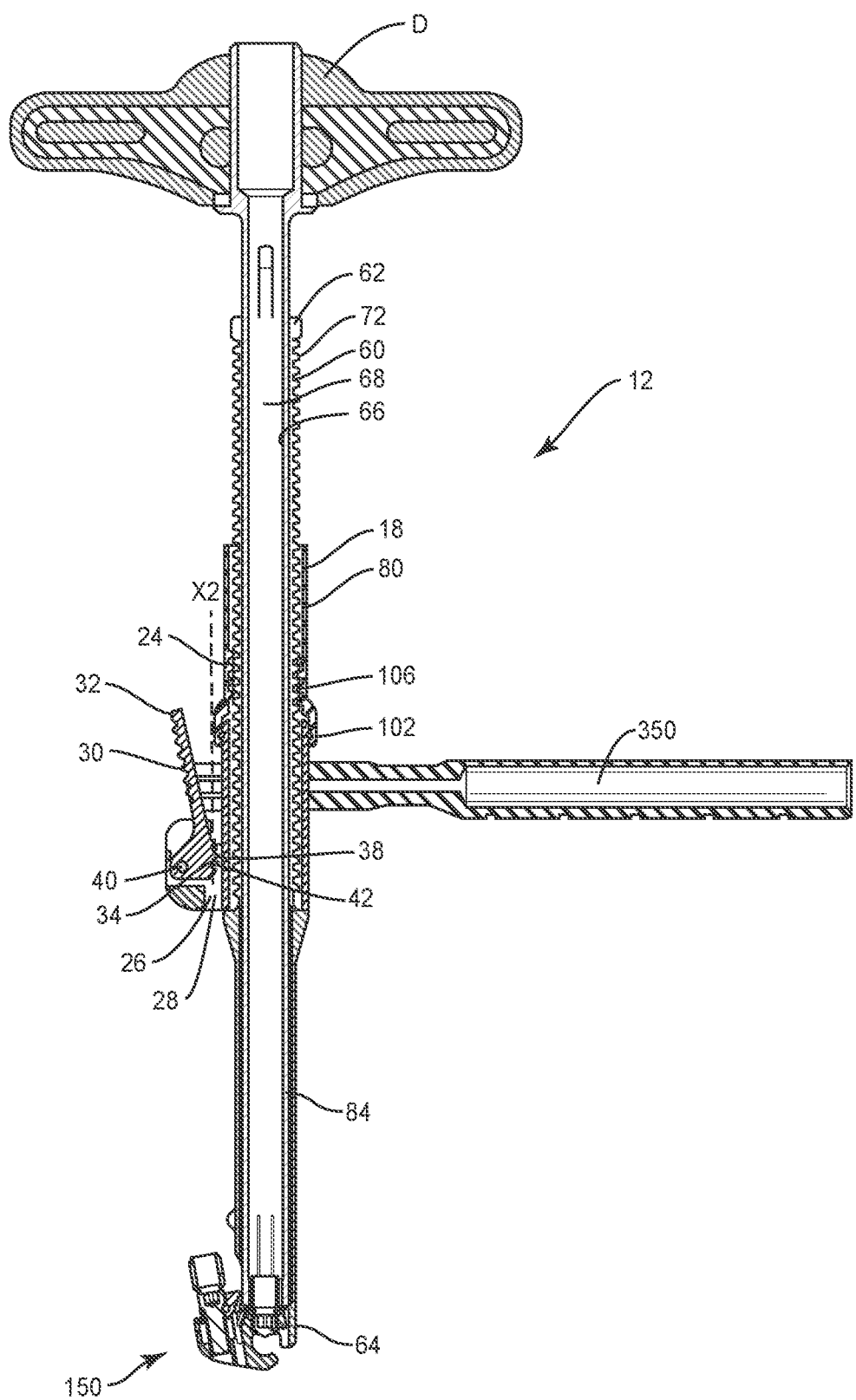
FIG. 2 is a cross section view of one embodiment of components of a surgical system in accordance with the principles of the present disclosure.
Figure 3:
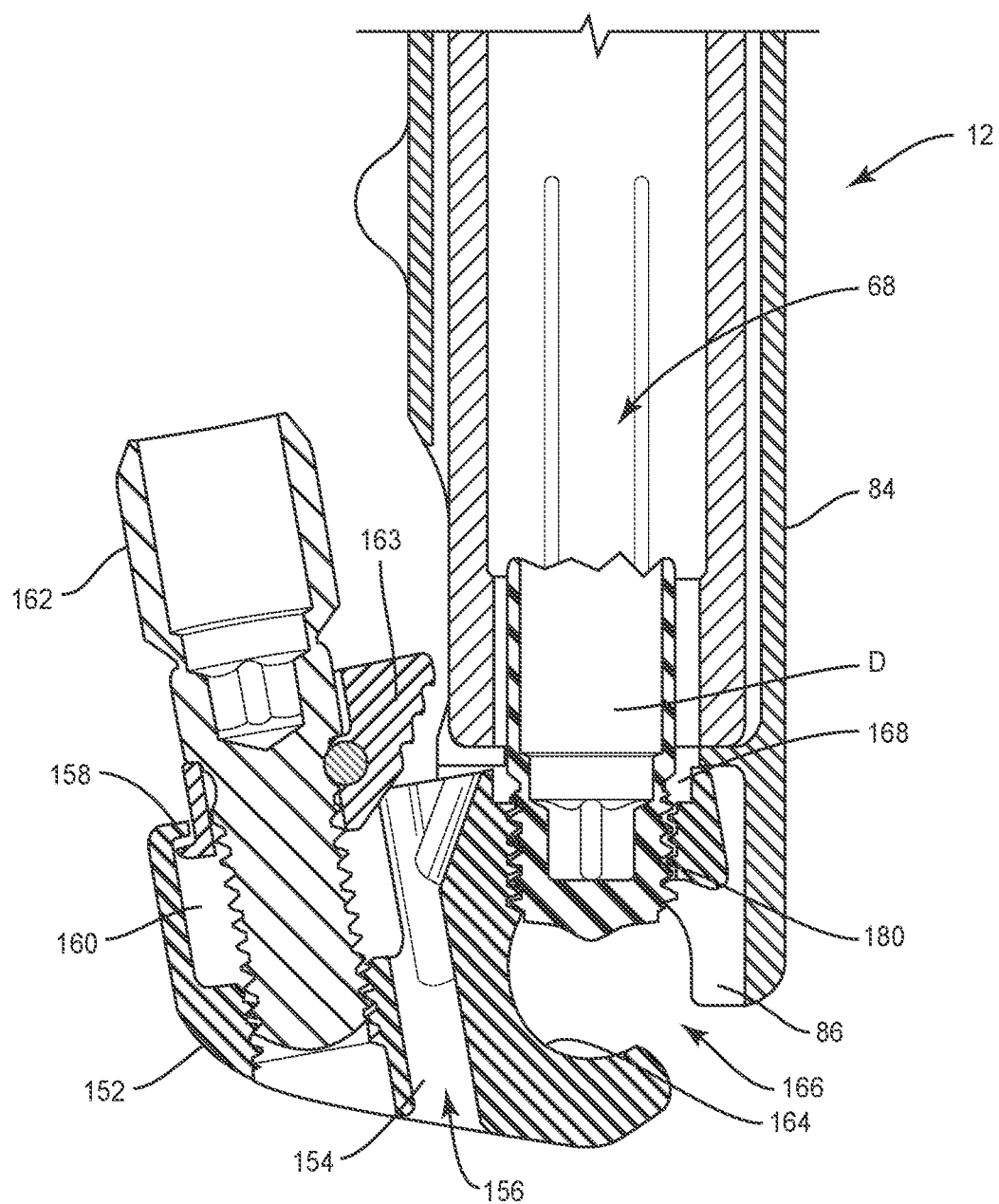
FIG. 3 is a break away view of the components shown in FIG. 2.
Figure 4:
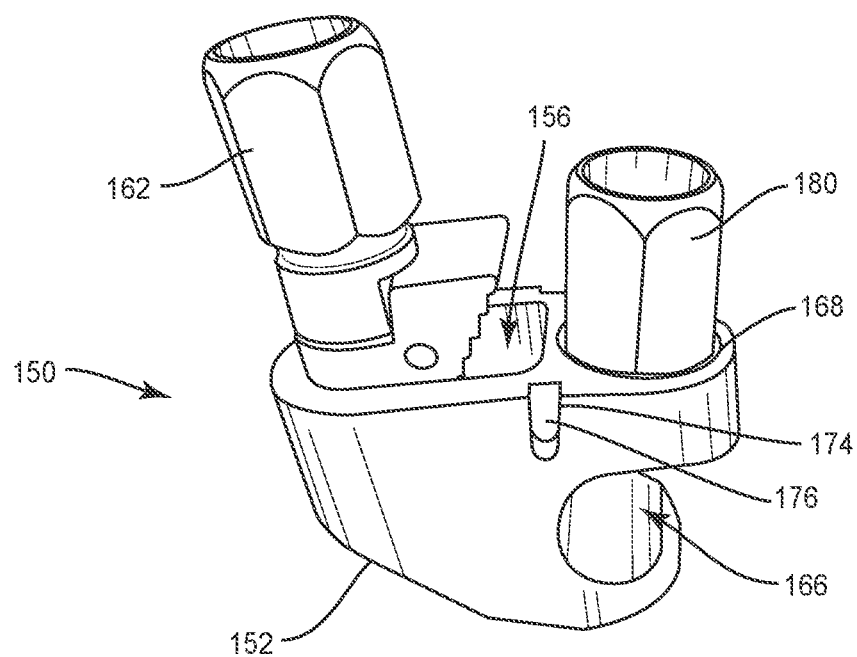
FIG. 4 is a perspective view of one embodiment of components of a surgical system in accordance with the principles of the present disclosure.
Figure 5:
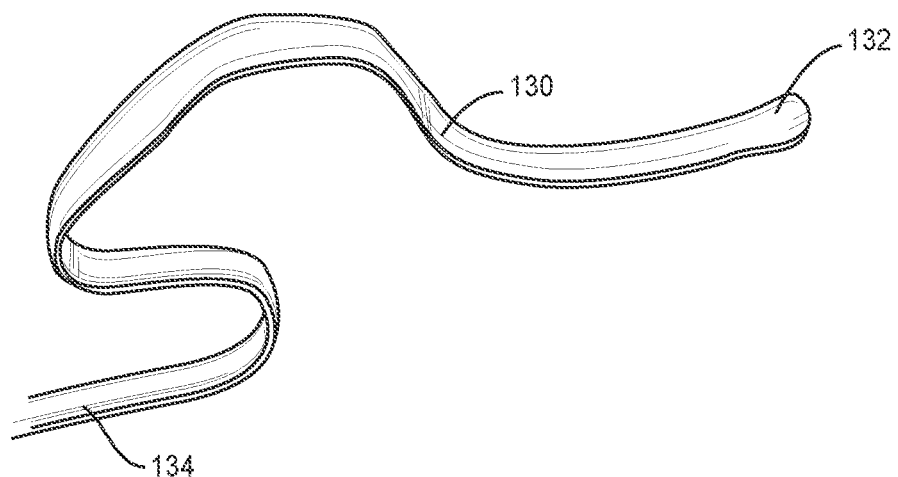
FIG. 5 is a perspective view of one embodiment of components of a surgical system in accordance with the principles of the present disclosure.

Carriage 18 includes a surface 26 that defines an elongated cavity, such as, for example, a pathway 28. Pathway 28 is configured for disposal of a longitudinal member, such as, for example, a tether 130. In some embodiments, pathway 28 extends along an axis X2, as shown in FIG. 2. In some embodiments, axis X2 is parallel to axis X1. In some embodiments, axis X2 extends transverse to axis X1. In some embodiments, pathway 28 may have various cross sectional and/or axial configurations, for example, square, oval, rectangular, polygonal, irregular, offset, staggered, uniform and non-uniform.

Carriage 18 includes an arm, such as, for example, a lever 30. Lever 30 extends between an end 32 and an end 34. End 34 includes a rotatable cam, such as, for example, a locking surface 38. Lever 30 is configured to pivot relative to axis X2 about a pin 40 disposed with end 34. Pin 40 is configured to facilitate engagement of locking surface 38 with tether 130. Locking surface 38 is in communication with pathway 28 such that locking surface 38 engages tether 130 to resist and/or prevent disengagement of tether 130 from pathway 28. In some embodiments, locking surface 38 is angled to facilitate engagement of tether 130 in a locked orientation, as described herein. In some embodiments, locking surface 38 may include penetrating members, such as, for example, a plurality of teeth 42. In some embodiments, teeth 42 may have various configurations, for example, round, oval, rectangular, polygonal, irregular, tapered, offset, staggered, uniform and non-uniform.

Rotation of lever 30 causes locking surface 38 to pivot between a non-locked orientation and a locked orientation with tether 130. In the non-locked orientation, tether 130 is movable relative to locking surface 38 such that tether 130 can translate along pathway 28 relative to one or more components of tensioner 12. In the locked orientation, teeth 42 engage tether 130 to fix tether 130 with carriage 18. Locking surface 38 applies a compressive force and/or a friction force, as described herein, to fix tether 130 in the locked orientation. Locking surface 38 is configured for engagement with tether 130 to resist and/or prevent disengagement of tether 130 from pathway 28. In some embodiments, lever 30 includes an enlarged engagement surface 40 configured to facilitate pivoting of lever 30. In some embodiments, lever 30 includes a shorter length to adjust a mechanical advantage of lever 30

Tensioner 12 includes a member, such as, for example, a surgical instrument guide 60 that extends between an end 62 and an end 64. Guide 60 includes a surface 66 that defines a cavity, such as, for example, a channel 68. Channel 68 is configured for disposal of a surgical instrument, such as, for example a surgical driver, as described herein, to facilitate engagement of a coupling member 180 with a spinal implant, such as, for example, a connector 150. In some embodiments, guide 60 includes channel 68, which comprises an axially-aligned passageway along the length of guide 60 such that the surgical driver can be inserted therethrough for engaging and tightening a coupling member, as described herein. In some embodiments, guide 60 includes channel 68 for disposal of a surgical driver to directly engage an implant, for example, a bone fastener, fixation element, plate or connector. In some embodiments, channel 68 may have various cross section and/or axial configurations, for example, round, oval, rectangular, polygonal, irregular, tapered, offset, staggered, arcuate, uniform and non-uniform.

In some embodiments, coupling member 180 includes a break off head (not shown). In some embodiments, the break off head includes a tool engaging portion configured to engage a surgical tool or instrument such as, for example, a surgical driver. In some embodiments, the break off head is frangibly connected with a body of coupling member 180. In some embodiments, the break off head is fabricated from a fracturing and/or frangible material such that manipulation of the head can fracture and separate the head at a predetermined force and/or torque limit, as described herein. In some embodiments, as force and/or torque is applied to the break off head and resistance increases, for example, due to fixation of threads coupling member 180 with connector 150, as described herein, the predetermined torque and force limit is approached.

In some embodiments, the break off head can fracture and separate at a predetermined force or torque limit, which may be in a range of approximately 9 Newton meters (Nm) to 12.5 Nm. In some embodiments, the break off head may be fabricated from a homogenous material or heterogeneously fabricated from different materials, and/or alternately formed of a material having a greater degree, characteristic or attribute of plastic deformability, frangible property and/or break away quality to facilitate fracture and separation of the head. In some embodiments, the break off head includes an inner diameter that facilitates a desired breakoff torque.

Guide 60 includes an outer surface 70 that includes a threaded surface 72. Threaded surface 72 extends between an end 74 and an end 76. In some embodiments, threaded surface 72 is continuous along surface 70. In some embodiments, threaded surface 72 includes a triple thread turn, spaced apart threads or a plurality of discrete threads. In some embodiments, threaded surface 72 includes one or more racks, as described herein. In some embodiments, indicia, such as, for example, hash marks are disposed on surface 70 to provide reference of dimension, such as, for example, length, depth and/or height.

Threaded surface 72 is configured for engagement with an actuator, such as, for example, a knob 80, as described herein. Guide 60 includes a circumferential flange 82 that movably supports knob 80. Guide 60 includes a sleeve 84 having one or more capture elements, such as, for example, a capture element 86 and a capture element 88 disposed at an end 64. Elements 86, 88 are configured for releasable engagement with connector 150. Elements 86, 88 each include an inner surface that define an implant cavity configured for disposal of at least a portion of connector 150, as described herein. The inner surfaces of elements 86; 88 include at least one fixation surface, such as, for example, inward tab projections (not shown) respectively, configured to releasably capture connector 150. The projections extend axially along sleeve 84.

Knob 80 includes a surface 100 configured to facilitate gripping and rotation of knob 80. In some embodiments, surface 100 may have alternate surface configurations, such as, for example, grooved, rough, threaded for connection with surgical instruments, arcuate, undulating, porous, semi-porous; dimpled, polished and/or textured. In some embodiments, knob 80 includes a surface, such as, for example, a tool engaging surface 102. Tool engaging surface 102 is configured for a mating engagement with a tool, such as, for example, a socket driver, as described herein. In some embodiments, tool engaging surface 102 includes configurations, such as, for example, triangular, square, polygonal, hexalobular, star or torx.

Figure 22:
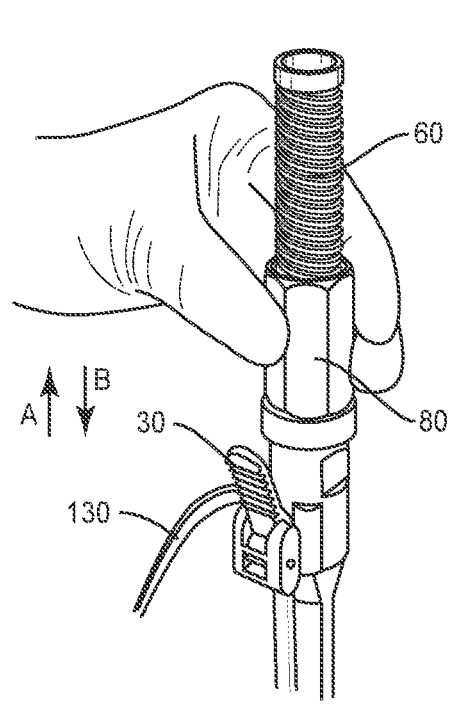
FIG. 22 is a perspective view of one embodiment of components of a surgical system in accordance with the principles of the present disclosure.

A threaded inner surface 106 of knob 80 engages threaded surface 72 such that knob 80 is rotatable relative to flange 82 to axially translate guide 60, in a direction shown by arrow A and a direction shown by arrow B in FIG. 22, relative to carriage 18. Knob 80 is rotatable in a clockwise and a counter clockwise direction to facilitate axial translation of carriage 18 relative to guide 60. Translation of carriage 18 relative to guide 60 causes an increase and/or a decrease in tension and/or tensile force in tether 130, as described herein. In some embodiments, carriage 18 is translated relative to guide 60 to incrementally increase and/or decrease tension in tether 130. In some embodiments, carriage 18 is translated relative to guide 60 to continuously increase and/or decrease tension in tether 130.

Tether 130 is a flexible longitudinal element that extends between an end 132 and an end 134. Tether 130 is configured for engagement with connector 150, as described herein. In some embodiments, end 132 and end 134 form a loop configured to surround all or a portion of tissue, such as, for example, laminae and/or a spinal implant, such as, for example, a spinal rod 170, as described herein. Tether 130 is configured for tensioning about a targeted portion of an anatomy of a body for attachment of tether 130 with the targeted portion of the anatomy, as described herein. In some embodiments, the targeted portion of the anatomy may include laminae, transverse process and/or pedicle regions of a vertebral level. In some embodiments, spinal correction system 10 may include one or a plurality of tethers 130, each tether being configured for disposal about a single and separate vertebral level. In some embodiments, a single vertebral level may include one or a plurality of tethers 130.

Tether 130 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, the flexibility of tether 130 includes movement in a lateral or side to side direction and prevents expanding and/or extension in an axial direction upon tensioning and attachment with a targeted portion of the anatomy. In some embodiments, all or only a portion of tether 130 may have a semi-rigid, rigid or elastic configuration, and/or have elastic properties, similar to the material examples described above, such that tether 130 provides a selective amount of expansion and/or extension in an axial direction. In some embodiments, tether 130 may be compressible in an axial direction. Tether 130 can include a plurality of separately attachable or connectable portions or sections, such as bands or loops, or may be monolithically formed as a single continuous element.

Tether 130 can have a uniform thickness/diameter. In some embodiments, tether 130 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 130 may be uniformly increasing or decreasing, or have alternate diameter dimensions along its length. In some embodiments, tether 130 may have various cross section configurations, such as, for example, oval, oblong, triangular, rectangular, square, polygonal, irregular, uniform, non-uniform, variable and/or tapered. In some embodiments, the surface of tether 130 may include engaging structures, such as, for example, barbs, raised elements and/or spikes to facilitate engagement with tissue of the targeted anatomy.

In some embodiments, tether 130 may have various lengths. In some embodiments, tether 130 may be braided, such as a rope, or include a plurality elongated elements to provide a predetermined force resistance. In some embodiments, tether 130 may be made from autograft and/or allograft, and be configured for resorbable or degradable applications. In some embodiments, tether 130 is a cadaver tendon. In some embodiments, tether 130 is a tendon that may be harvested, for example, from a patient or donor. In some embodiments, a tendon harvested from a patient may be affixed in remote locations with the patient's body.

Spinal correction system 10 includes connector 150. Connector 150 includes a body 152 having a surface 154 that defines a cavity, such as, for example, a passageway 156 configured for disposal of tether 130. In some embodiments, passageway 156 may have various cross section configurations, such as, for example, oval, oblong, triangular, rectangular, square, polygonal, irregular, uniform, non-uniform, variable and/or tapered. In some embodiments, surface 154 may include gripping elements or surfaces, such as, for example, rough, arcuate, undulating, mesh, porous, semi-porous, dimpled and/or textured to facilitate engagement with tether 130. Body 152 includes a surface 158 that defines a cavity, such as, for example, an opening 160. Opening 160 is configured for disposal of a coupling member, such as, for example, a set screw 162.

Body 152 includes a surface 164 that defines a passageway 166. Passageway 166 has an oblong configuration and extends transversely through body 152. In some embodiments, passageway 166 may have alternate cross section configurations, such as, for example, oval, cylindrical, triangular, square, polygonal, irregular, uniform, non-uniform, offset, staggered, undulating, arcuate, variable and/or tapered. Passageway 166 is configured for disposal of spinal rod 170 such that connector 150 can be mounted with spinal rod 170, as described herein. Body 152 includes an opening 168. Opening 168 is configured for engagement with a coupling member, such as, for example, a set screw 180 to fix rod 170 with connector 150, as described herein.

Body 152 includes a mating surface 174 that defines cavities, such as, for example, mating slots 176 configured to mate with the projections of sleeve 84 to facilitate connection of tensioner 12 with connector 150. As such, guide 60 is connected with connector 150 and channel 68 is axially aligned with set screw 180. This configuration facilitates disposal of a surgical driver with channel 68 such that the surgical driver is guided along channel 68 into an orientation for engagement with set screw 180 for tightening and fixation of spinal rod 170 with connector 150, as described herein. In some embodiments, spinal correction system 10 may include one or a plurality of implant connectors spaced apart and disposed along a spinal implant, such as, for example, spinal rod 170, which may be relatively disposed in a side by side, irregular, uniform, non-uniform, offset and/or staggered orientation or arrangement, along one or a plurality of spinal rods. In some embodiments, spinal rod 170 extends along one or a plurality of vertebra, as described herein. In some embodiments, spinal correction system 10 may include one or a plurality of spinal rods 170, which may be relatively disposed in a side by side, irregular, uniform, non-uniform, offset and/or staggered orientation or arrangement.

In assembly, operation and use, spinal correction system 10, similar to the systems and methods described herein, is employed with a surgical procedure, such as, for example, a correction treatment of an affected portion of a spine, which may include a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. Spinal correction system 10 may be completely or partially revised, removed or replaced.

In use, to treat a selected section of vertebrae V, as shown in FIGS. 6-31, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Figure 6:
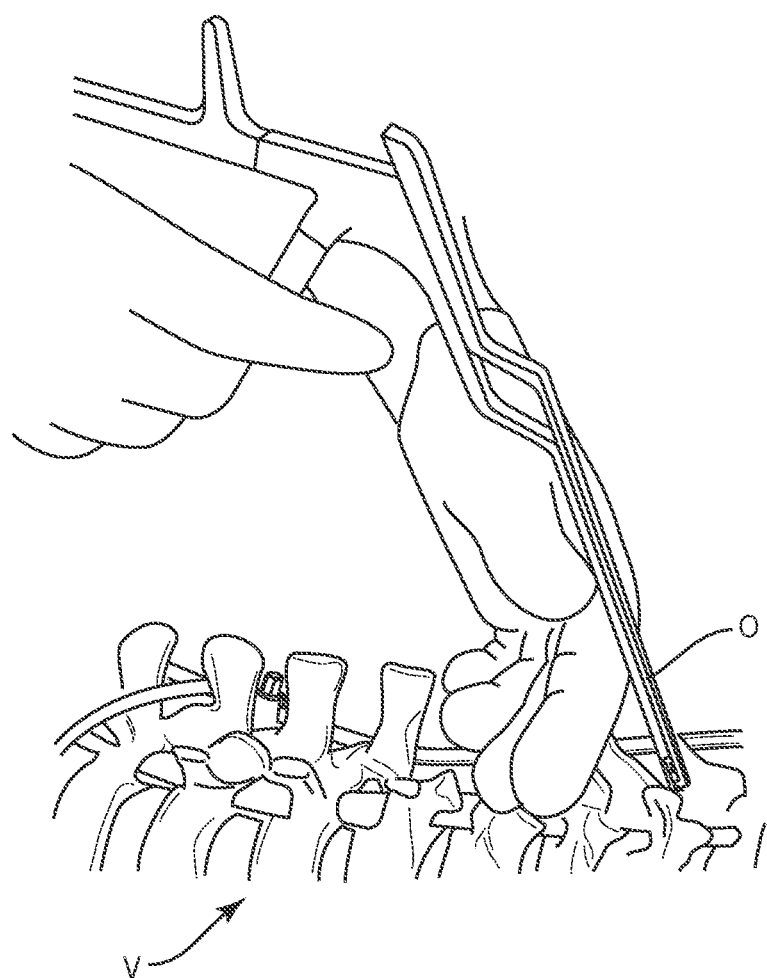
FIG. 6 is a perspective view of one embodiment of components of a surgical system in accordance with the principles of the present disclosure disposed with vertebrae.
Figure 7:
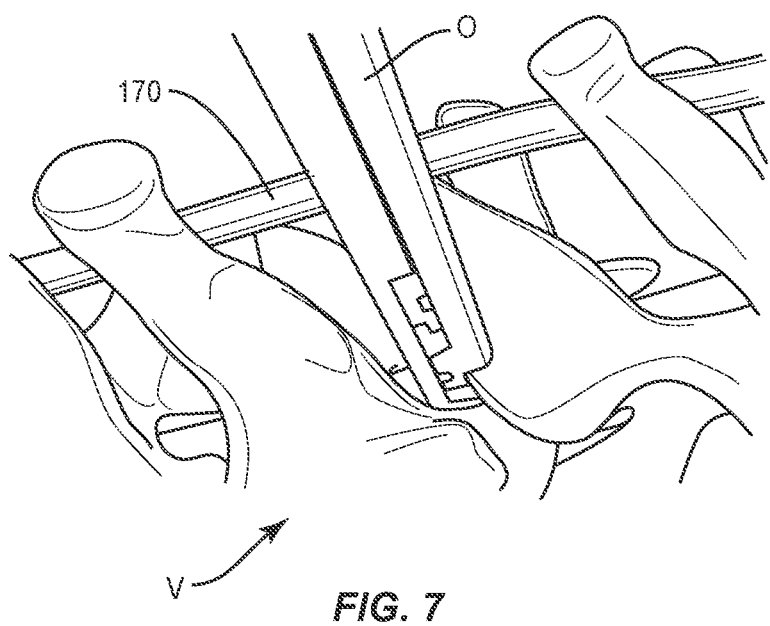
FIG. 7 is a perspective view of one embodiment of components of a surgical system in accordance with the principles of the present disclosure disposed with vertebrae.

A surgical instrument, such as, for example, an osteotome O is utilized to prepare tissue surfaces, such as, for example, laminae for disposal of tether 130 therewith, as shown in FIGS. 6 and 7. End 132 of tether 130 is threaded through passageway 156 of connector 150, as shown in FIGS. 8 and 9. Screw 162 is disposed in a non-locked orientation such that tether 130 is movable within passageway 156 and a cleat 163 is positioned therein.

Figure 11:
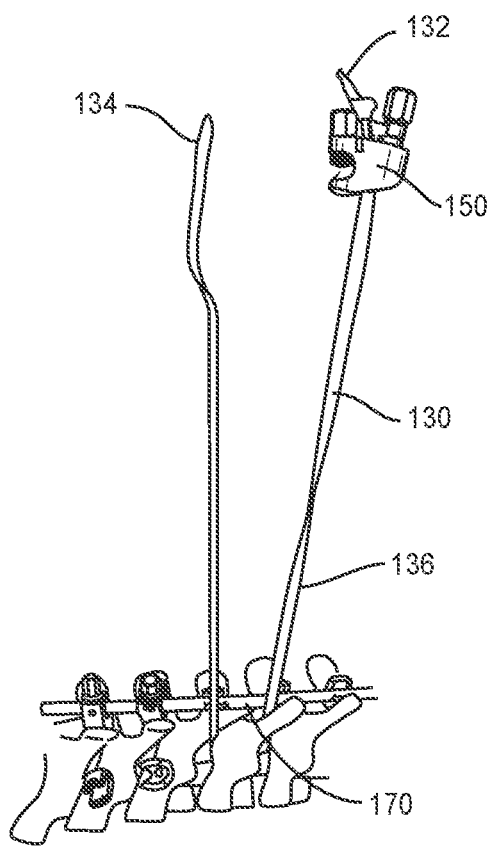
FIG. 11 is a perspective view of one embodiment of components of a surgical system in accordance with the principles of the present disclosure disposed with vertebrae.
Figure 12:
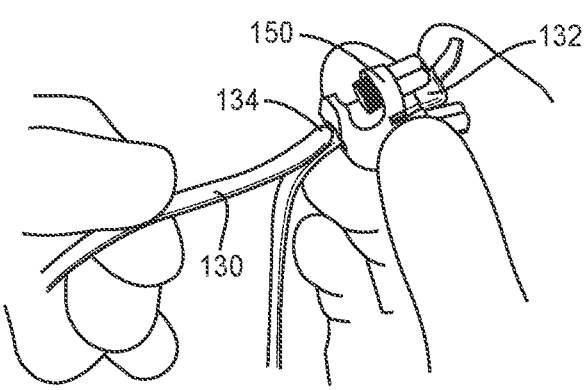
FIG. 12 is a perspective view of one embodiment of components of a surgical system in accordance with the principles of the present disclosure disposed with vertebrae.
Figure 13:
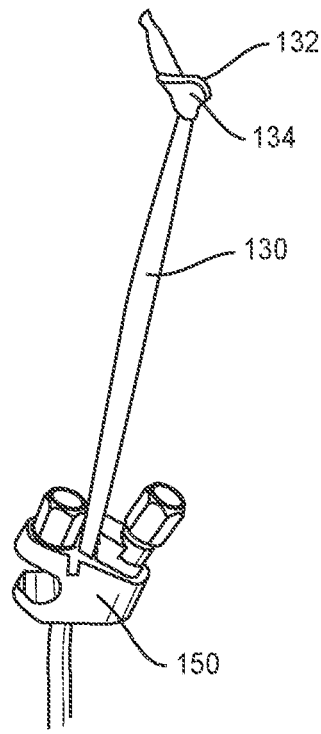
FIG. 13 is a perspective view of one embodiment of components of a surgical system in accordance with the principles of the present disclosure disposed with vertebrae.
Figure 14:
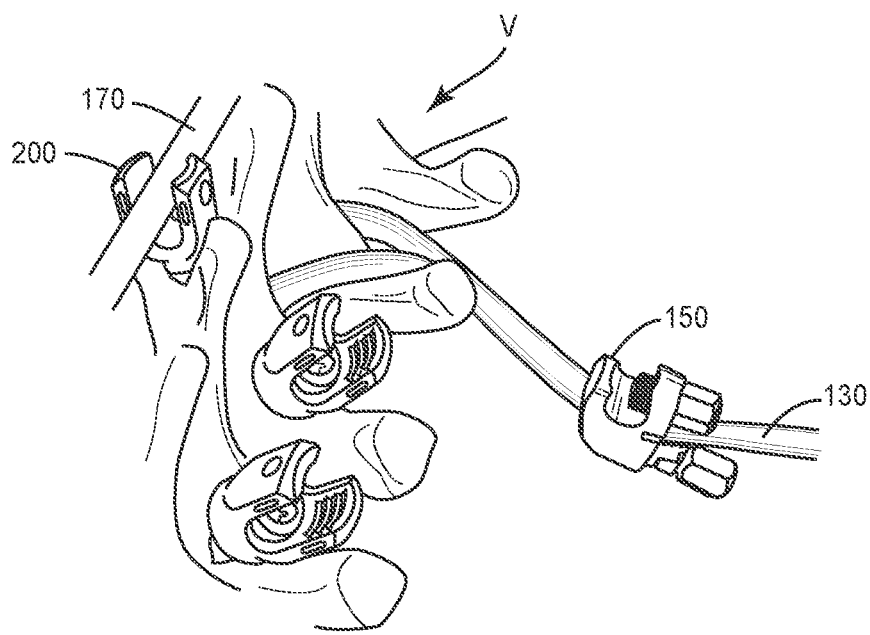
FIG. 14 is a perspective view of one embodiment of components of a surgical system in accordance with the principles of the present disclosure disposed with vertebrae.
Figure 15:
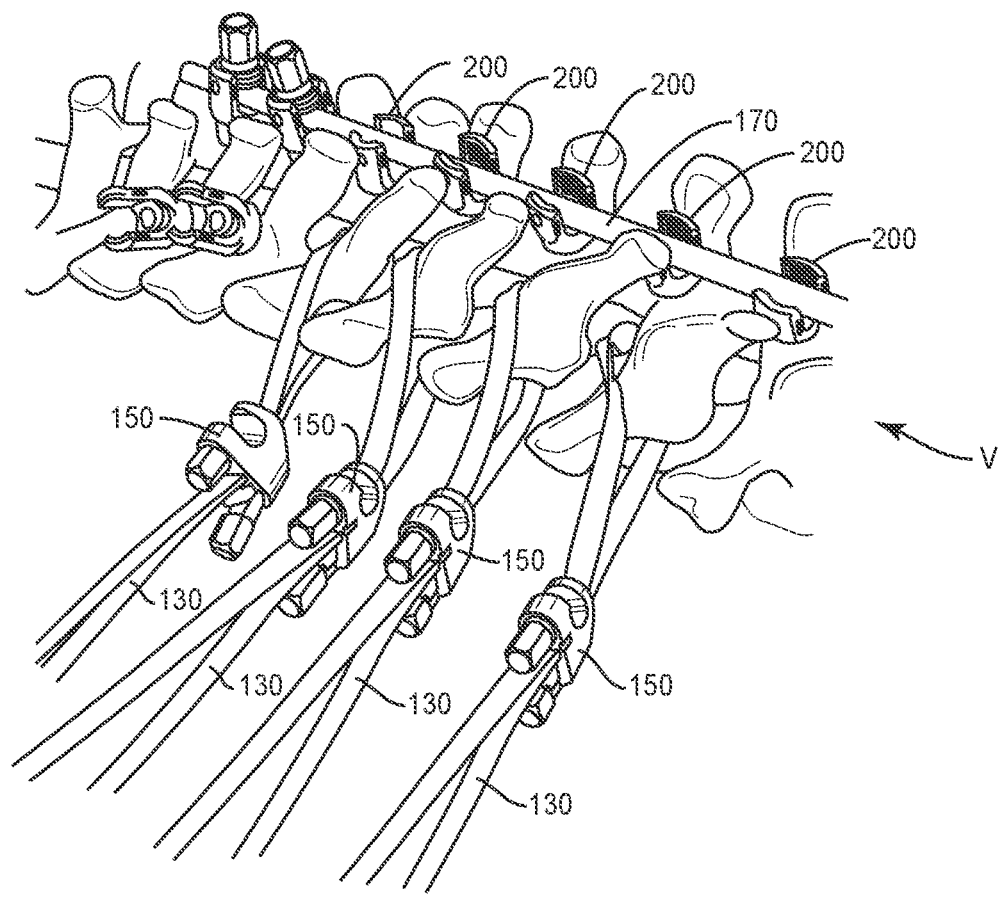
FIG. 15 is a perspective view of one embodiment of components of a surgical system in accordance with the principles of the present disclosure disposed with vertebrae.
Figure 16:
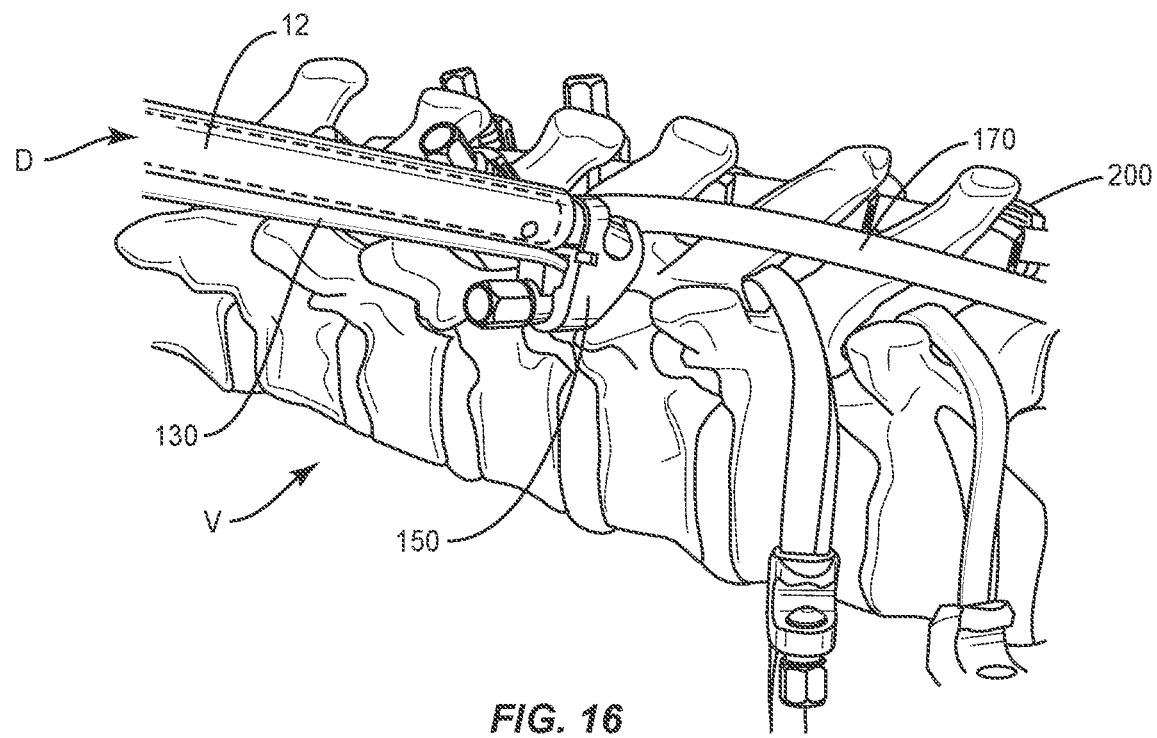
FIG. 16 is a perspective view of one embodiment of components of a surgical system in accordance with the principles of the present disclosure disposed with vertebrae.
Figure 17:
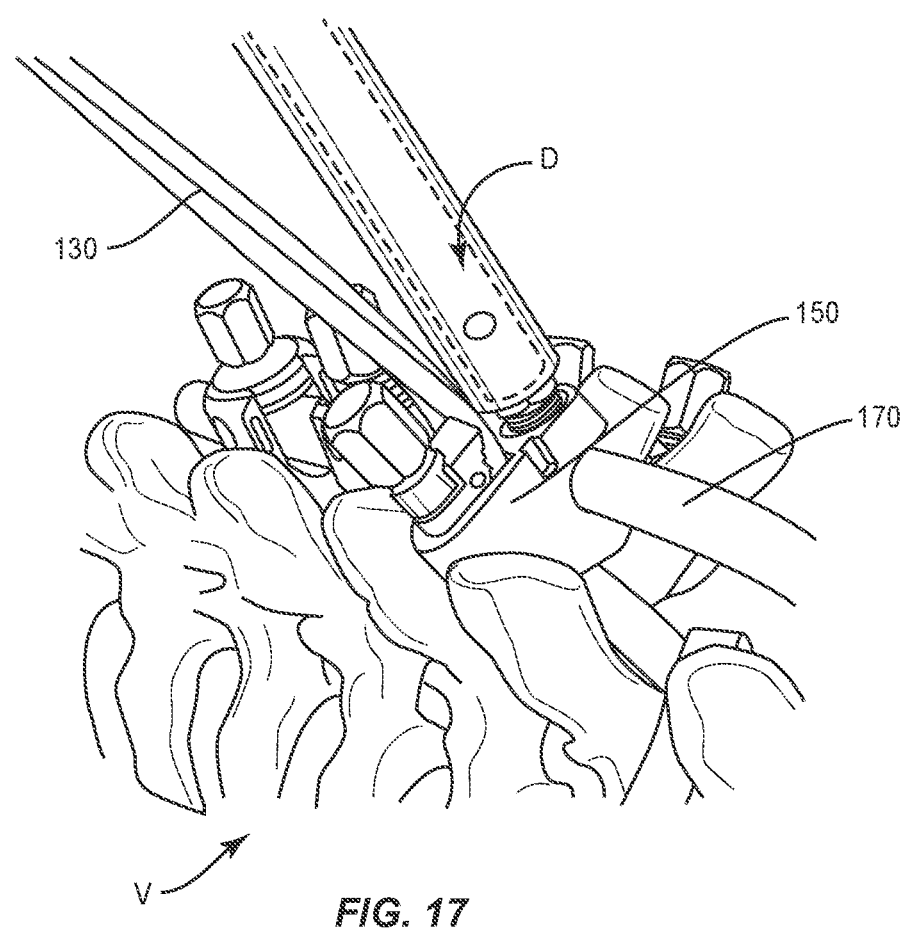
FIG. 17 is a perspective view of one embodiment of components of a surgical system in accordance with the principles of the present disclosure disposed with vertebrae.
Figure 18:
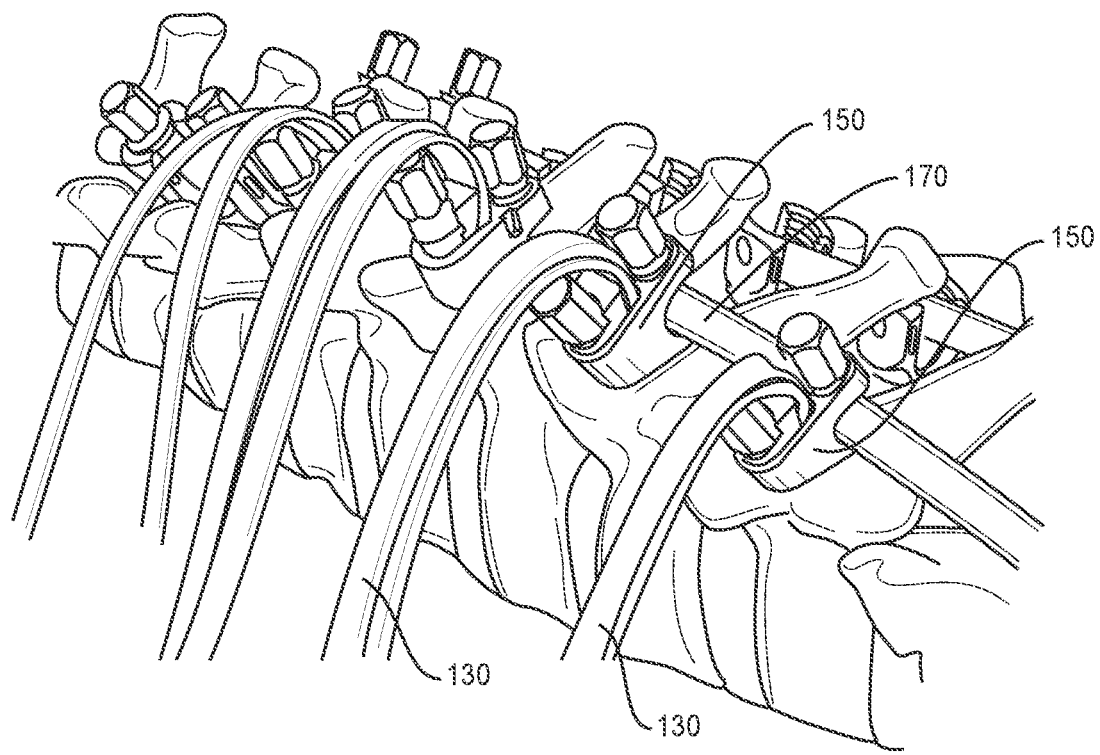
FIG. 18 is a perspective view of one embodiment of components of a surgical system in accordance with the principles of the present disclosure disposed with vertebrae.
Figure 19:
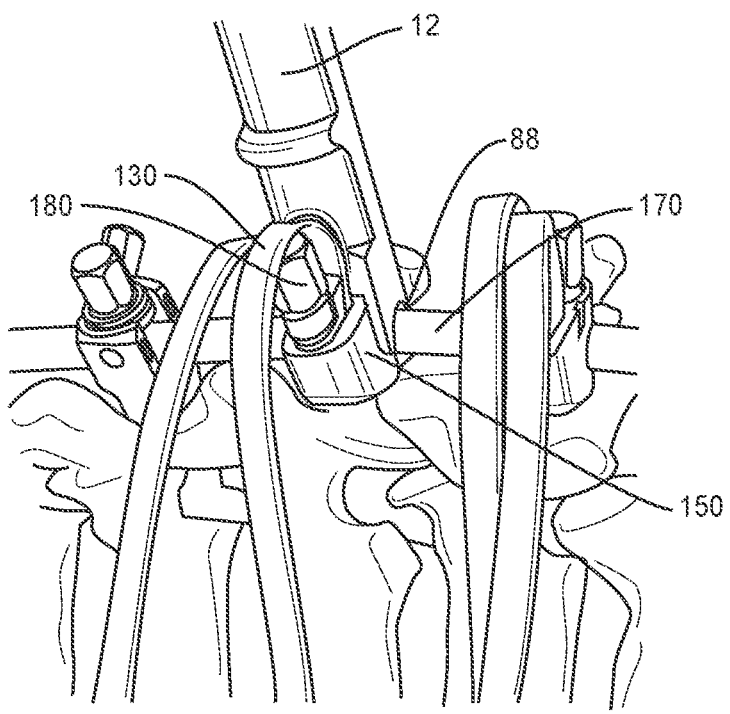
FIG. 19 is a perspective view of one embodiment of components of a surgical system in accordance with the principles of the present disclosure disposed with vertebrae.

Pilot holes are made in vertebrae V in a selected orientation. Bone fasteners 200 are aligned with the pilot holes and fastened with the tissue of vertebrae V, as shown in FIG. 10. Tether 130 and connector 150 are delivered along the surgical pathway to a surgical site adjacent a lateral side of vertebrae V, and tether 130 is disposed with vertebrae V and/or spinal rod 170, as shown in FIG. 11. In one embodiment, a loop 136 of tether 130 is disposed about a transverse process of a vertebra. This configuration fixes and/or attaches tether 130 with the transverse process and/or lamina. In some embodiments, connector 150 is oriented medially and end 134 of tether 130 is threaded through passageway 156 for connection with connector 150, as shown in FIGS. 12-14. In some embodiments, additional tethers 130 and/or connectors 150 are engaged along multiple vertebral levels, as shown in FIG. 15.

Spinal rod 170 is disposed with bone fasteners 200. Spinal rod 170 is seated with connectors 150, as shown in FIGS. 16-19. Tensioner 12 is disposed adjacent connector 150 and sleeve 84 is connected with connector 150 such that the projections engage mating slots 176, as described herein. Guide 60 is connected with connector 150 and channel 68 is axially aligned with set screw 180 such that a surgical driver D is disposed with channel 68. Driver D is guided along channel 68 into an orientation for engagement with set screw 180 for tightening and fixation of spinal rod 170 with connectors 150, as described herein. Set screws 180 are individually engaged by driver D and rotated to provisionally fix connectors 150 with spinal rod 170.

Figure 20:
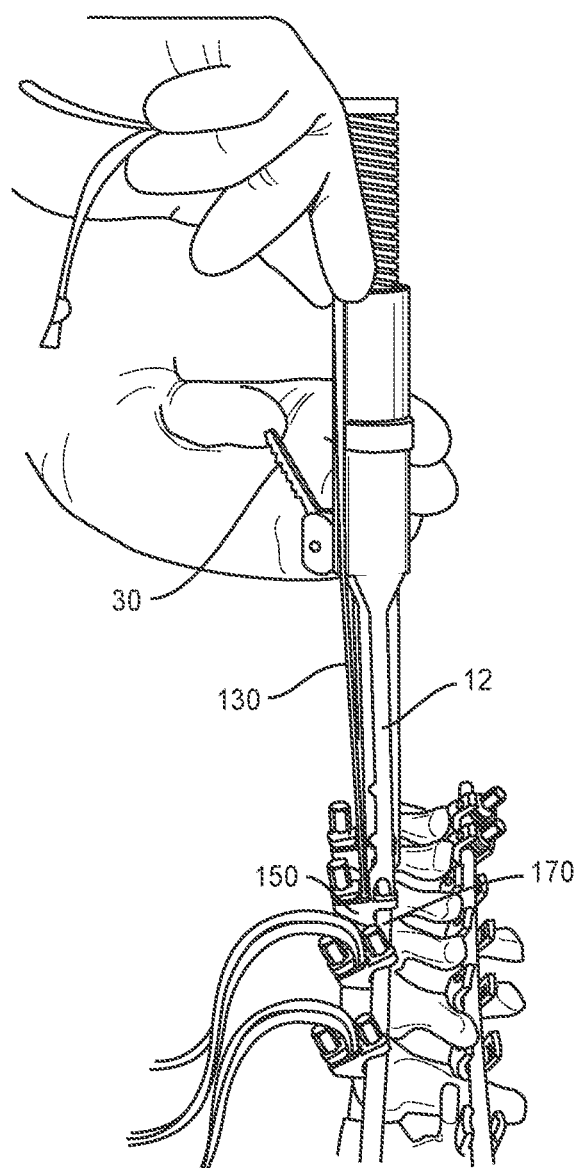
FIG. 20 is a perspective view of one embodiment of components of a surgical system in accordance with the principles of the present disclosure disposed with vertebrae.
Figure 21:
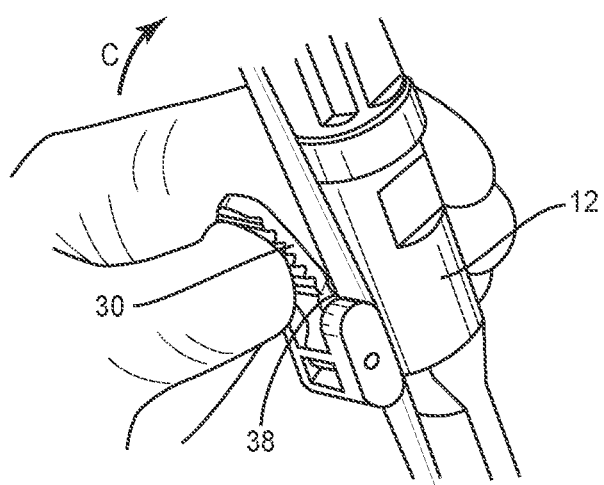
FIG. 21 is a perspective view of one embodiment of components of a surgical system in accordance with the principles of the present disclosure.

Tether 130 is threaded through pathway 28 of tensioner 12 and lever 30 is disposed in the non-locked orientation with tether 130, as shown in FIG. 20. Lever 30 is actuated to pivot, in a direction shown by arrow C in FIG. 21, such that locking surface 38 engages tether 130, as described herein, to dispose lever 30 in the locked orientation with tether 130. Locking surface 38 applies a compression force to tether 130 to resist and/or prevent tether 130 from freely translating and/or disengaging from pathway 28.

Knob 80 is rotated to axially translate guide 60, as described herein. Knob 80 is rotatable in a counter clockwise direction to facilitate axial translation of carriage 18 relative to guide 60, in a direction shown by arrow A in FIG. 22, to cause an increase in tension and/or tensile force in tether 130, as described herein. Knob 80 is rotatable in a clockwise direction to facilitate axial translation of carriage 18 relative to guide 60, in a direction shown by arrow B in FIG. 22, to cause a decrease in tension and/or tensile force in tether 130, as described herein.

Figure 23:
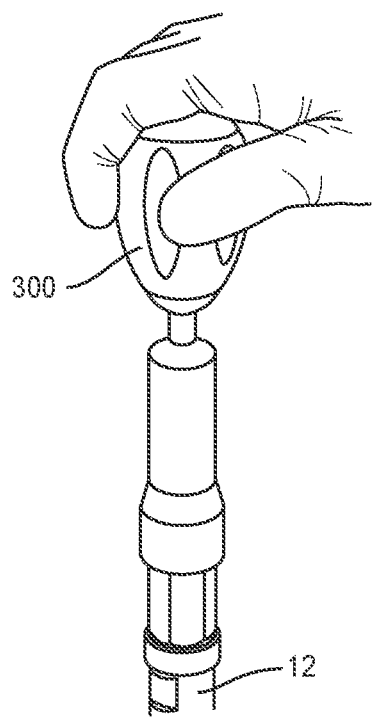
FIG. 23 is a perspective view of one embodiment of components of a surgical system in accordance with the principles of the present disclosure.
Figure 24:
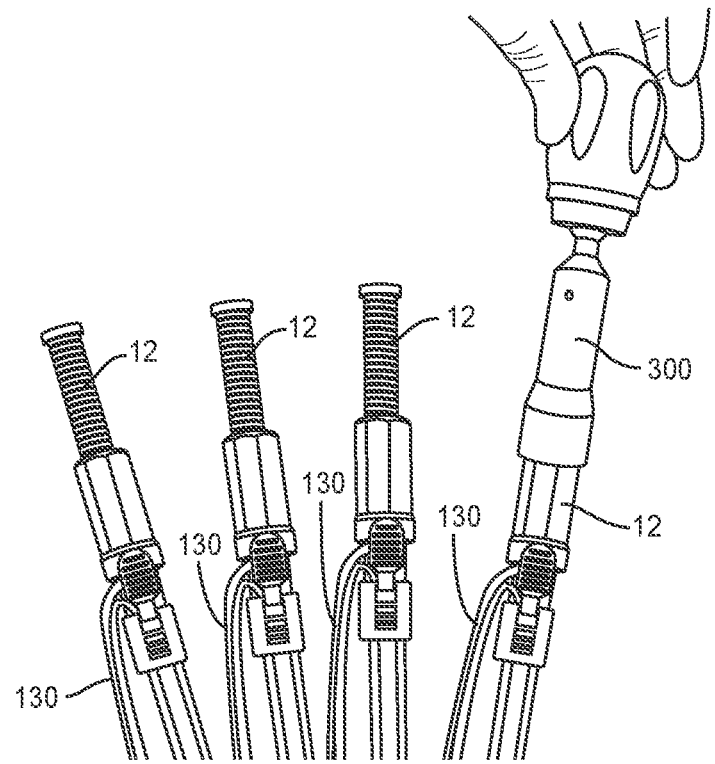
FIG. 24 is a perspective view of one embodiment of components of a surgical system in accordance with the principles of the present disclosure.

Translation of carriage 18, in a direction shown by arrow A in FIG. 22, draws tether 130 to apply a tensioning force to tether 130. This configuration tensions tether 130 about the vertebra and tensions the spinal construct for attachment with vertebrae V and/or to apply corrective treatment to vertebrae V. In some embodiments, the tension and/or tensile force applied to tether 130 and/or corrective forces applied to vertebrae V can be increased by further actuation of knob 80 to incrementally and/or selectively tension tether 130. In some embodiments, the tension and/or tensile force applied to tether 130 and/or corrective forces applied to vertebrae V can be increased and/or decreased by tensioner 12. In some embodiments, a T-handle instrument 300 is engaged with tensioner 12 and/or knob 80 to facilitate tightening of tether 130, as shown in FIG. 23. In some embodiments, tensioner 12 is utilized at various vertebral levels and a sequential tensioning is applied to translate vertebrae V towards spinal rod 170, as shown in FIG. 24.

Figure 25:
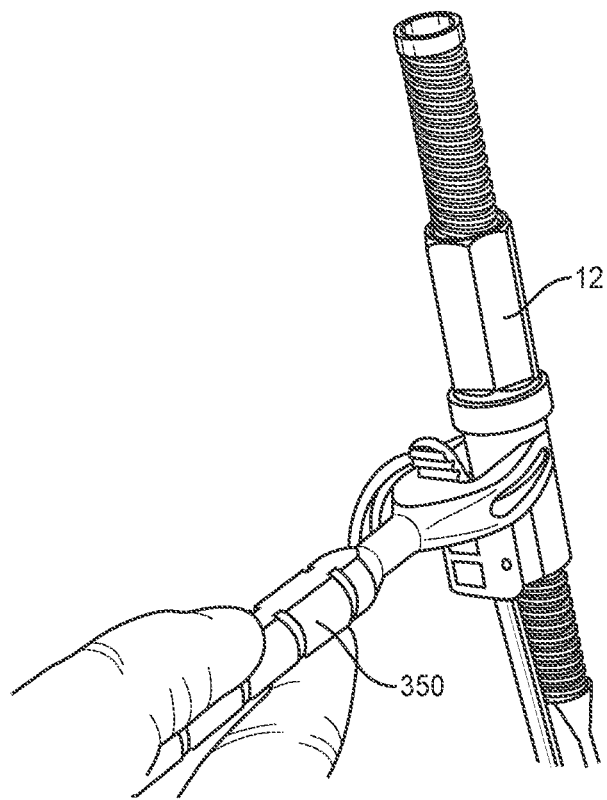
FIG. 25 is a perspective view of one embodiment of components of a surgical system in accordance with the principles of the present disclosure.
Figure 26:
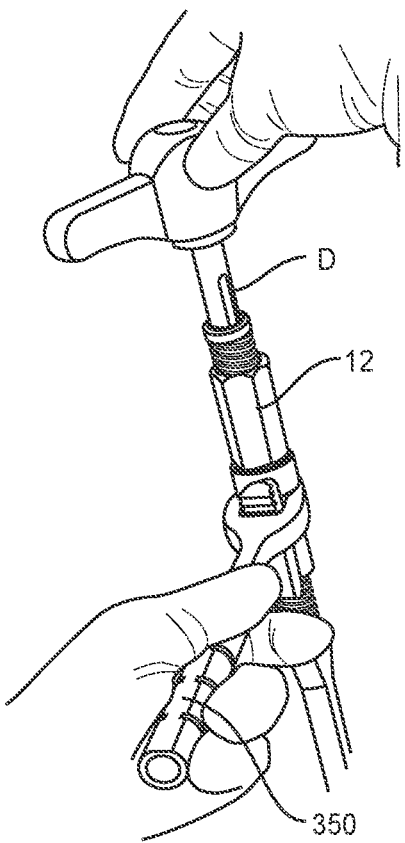
FIG. 26 is a perspective view of one embodiment of components of a surgical system in accordance with the principles of the present disclosure.

In some embodiments, a counter torque tool 350 is engaged with tensioner 12, as shown in FIGS. 25 and 26. Driver D is translated along channel 68 of guide 60 into engagement with set screw 180, as described herein. Driver D is rotated to finally tighten set screw 180 with connector 150 and spinal rod 170. Tool 350 includes bifurcated extensions that are disposed about the outer surface of tensioner 12. The extensions of tool 350 engage the outer surface of tensioner 12 to fix position and/or restrain tensioner 12 to resist and/or prevent rotation of tensioner 12 as driver D simultaneously tightens set screw 180 with connector 150 and spinal rod 170. In some embodiments, tool 350 is configured to provide additional leverage to facilitate removing and/or separating a frangible or break off portion of set screw 180 engaged with connector 150 at a selected torque limit.

Figure 27:
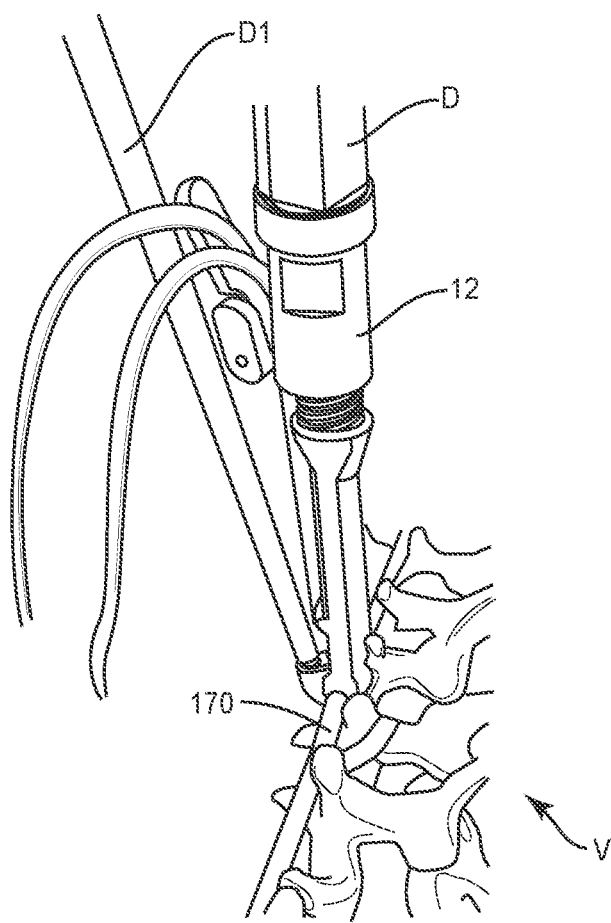
FIG. 27 is a perspective view of one embodiment of components of a surgical system in accordance with the principles of the present disclosure disposed with vertebrae.
Figure 28:
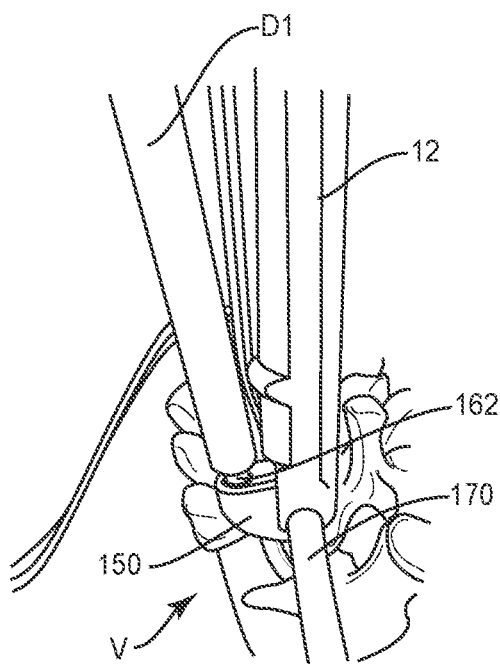
FIG. 28 is a perspective view of one embodiment of components of a surgical system in accordance with the principles of the present disclosure disposed with vertebrae.

Set screw 162 is actuated by a driver D1 by rotating screw 162 in a clockwise direction to engage cleat 163, as shown in FIGS. 27 and 28. Cleat 163 is translated within passageway 156 such that its teeth engage tether 130. Translation of cleat 163 applies a compressive force and/or a friction force to fix tether 130 in a locked orientation with connector 150. In some embodiments, a driver is rotatable to a predetermined force and/or torque limit to separate frangible portions of screw 162. This configuration fixes tension of tether 130 about vertebrae V and tensions components of the spinal construct for attachment with vertebrae V and/or to apply corrective treatment to vertebrae V.

Figure 29:
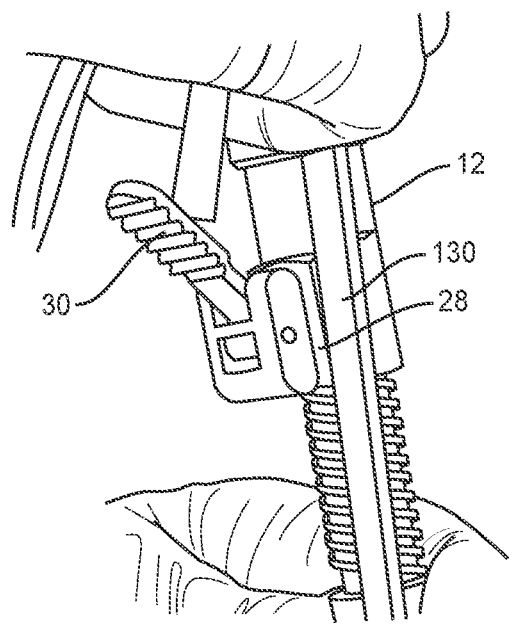
FIG. 29 is a perspective view of one embodiment of components of a surgical system in accordance with the principles of the present disclosure.
Figure 30:
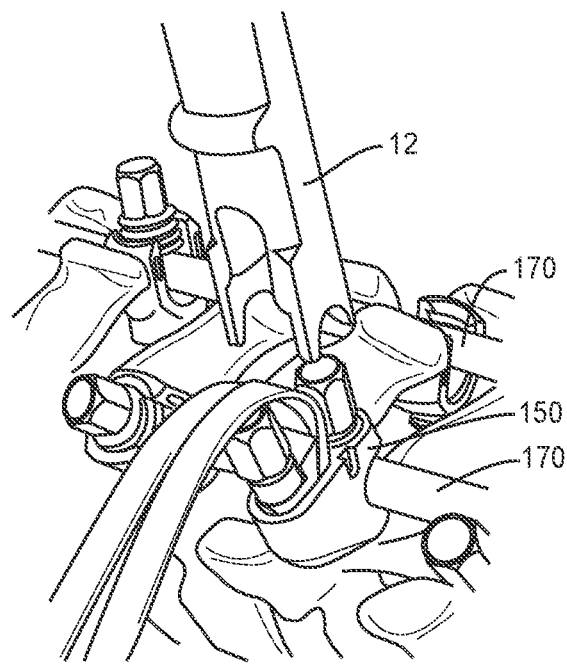
FIG. 30 is a perspective view of one embodiment of components of a surgical system in accordance with the principles of the present disclosure disposed with vertebrae.
Figure 31:
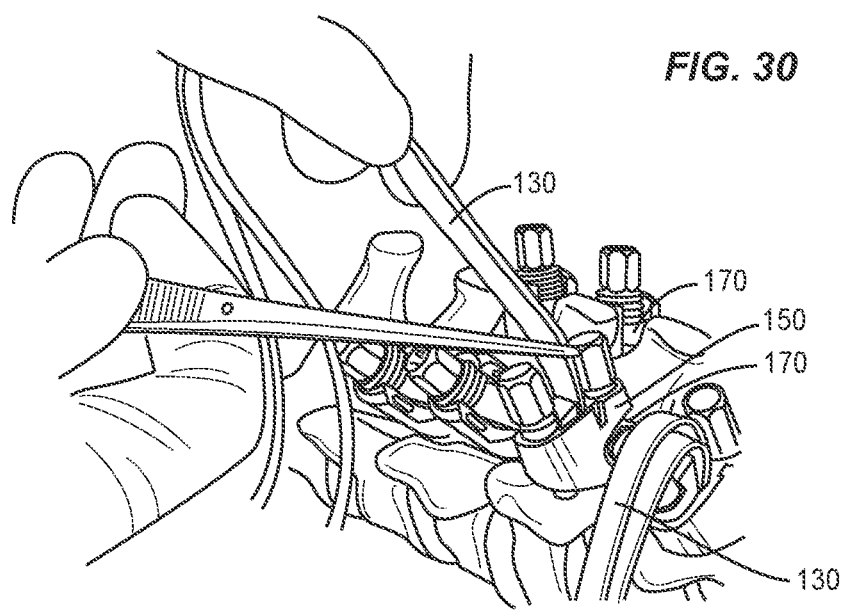
FIG. 31 is a perspective view of one embodiment of components of a surgical system in accordance with the principles of the present disclosure disposed with vertebrae.

To disengage tensioner 12 from connector 150, lever 30 is disposed in the non-locked orientation, as shown in FIG. 29. Locking surface 38 disengages from tether 130 to allow tether 130 to disengage and/or translate through pathway 28. The projections of sleeve 84 are released from connector 150, as shown in FIG. 30. Excess tether 130 is cut from connector 150, as shown in FIG. 31. In some embodiments, a tail of 5 mm of tether 130 remains and extends from connector 150.

In some embodiments, spinal implant system 10 includes a second spinal rod 170, as shown in FIGS. 30 and 31, delivered along the surgical pathway to the surgical site adjacent a contra-lateral side of vertebrae V. Second spinal rod 170 is connected with the contra-lateral side of vertebrae V via one or more tethers 130, similar to spinal rod 170 described herein. In some embodiments, spinal rod 170 and second spinal rod 170 are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters. Spinal implant system 10 may be completely or partially revised, removed or replaced.

Upon completion of the procedure, the surgical instruments, assemblies and non-implanted components of spinal correction system 10 are removed from the surgical site and the incision is closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10.

In some embodiments, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member defining a cavity and including a locking surface disposed with the cavity, the locking surface being engageable with a tether to fix the tether with the first member;
   a second member including an inner surface that defines a longitudinal passageway configured for disposal of a surgical driver;
   a coupling member positioned within the passageway;
   a connector comprising a body including spaced apart first and second arms that define a rod cavity therebetween, the connector comprising an opening extending through a thickness of one of the first arms, the coupling member extending through the opening to connect the connector with the coupling member; and
   an actuator defining a cavity having the second member positioned therein, the actuator being coaxial with the longitudinal passageway and configured to incrementally tension the tether.

2. A surgical instrument as recited in claim 1, wherein the second member comprises a driver guide.

3. A surgical instrument as recited in claim 1, further comprising the surgical driver, wherein the surgical driver is engageable with the coupling member, the coupling member having a break off portion.

4. A surgical instrument as recited in claim 1, wherein the actuator is threaded with the second member.

5. A surgical instrument as recited in claim 1, wherein:
   the connector comprises a second locking surface engageable with the tether to fix the tether with the connector; and
   the body defines a channel configured for disposal of the tether, the connector including a cleat configured to translate within the channel to fix the tether relative to the body, the cleat defining the second locking surface.

6. A surgical instrument as recited in claim 1, wherein the second member includes an outer sleeve and an inner sleeve.

7. A surgical instrument as recited in claim 1, wherein the second member extends between a first end and a second end, the first end being proximal to a proximal end of the actuator, the second end being distal to a distal end of the actuator.

8. A surgical instrument as recited in claim 1, wherein the second member comprises a circumferential flange that movably supports the actuator.

9. A surgical instrument as recited in claim 8, wherein the actuator is rotatable relative to the flange to axially translate the second member in a first axial direction and an opposite second axial direction relative to the first member.

10. A surgical instrument as recited in claim 1, wherein the body defines a channel configured for disposal of the tether, the channel being spaced apart from the rod cavity by a wall.

11. A surgical instrument as recited in claim 1, wherein the body defines a channel configured for disposal of the tether, the channel being spaced apart from the rod cavity by a wall such that the channel is not in communication with the rod cavity.

12. A surgical instrument as recited in claim 1, wherein the coupling member is axially aligned with the longitudinal passageway.

13. A surgical system comprising:
   a tether;
   a surgical instrument including a first member defining a cavity and including a locking surface disposed with the cavity, the locking surface being engageable with the tether to fix the tether with the first member,
   the surgical instrument further including a second member including an inner surface that defines a longitudinal passageway;
   an actuator connected with the members to incrementally tension the tether, the actuator defining a cavity having the second member positioned therein, the cavity of the actuator being coaxial with the longitudinal passageway;
   a coupling member positioned within the longitudinal passageway;
   a connector comprising a body including spaced apart first and second arms that define a C-shaped rod cavity therebetween, the connector comprising a threaded opening extending through a thickness of one of the arms, the coupling member extending through the threaded opening to connect the connector with the coupling member; and
   a surgical driver disposable with the longitudinal passageway and engageable with the coupling member.

14. A surgical system as recited in claim 13, wherein the second member comprises a driver guide.

15. A surgical system as recited in claim 13, wherein the coupling member is axially aligned with the longitudinal passageway.

16. A surgical system as recited in claim 13, wherein the coupling member has a break off portion.

17. A surgical system as recited in claim 13, further comprising a counter torque tool engageable with the surgical instrument, the counter torque tool comprising bifurcated extensions that are disposed about an outer surface of the first member to prevent rotation of the surgical instrument as the surgical driver simultaneously tightens the coupling member with the connector.

18. A method for treating a spine, the method comprising the steps of:
   delivering a spinal construct to a surgical site including vertebrae, the spinal construct including a connector configured for disposal of a tether and a spinal rod, the connector comprising a body including spaced apart first and second arms that define a rod cavity therebetween, the connector comprising a threaded opening extending through a thickness of one of the arms, the spinal construct further including a coupling member engageable with the spinal rod and the connector, the coupling member extending through the threaded opening to connect the connector with the coupling member;
   connecting the tether with the vertebrae;
   mating a surgical instrument with the connector, the surgical instrument including a first member having a locking surface being engageable with the tether, a second member that defines a longitudinal passageway and an actuator, the second member being positioned in a cavity of the actuator, the cavity of the actuator being coaxial with the longitudinal passageway;

rotating the actuator relative to the second member to move the second member axially relative to the first member and tension the tether with the surgical instrument; and guiding a surgical driver through the longitudinal passageway for connection with the coupling member.

19. A method for treating a spine as recited in claim 18, further comprising the step of engaging the surgical instrument with a counter torque handle.

20. A method for treating a spine as recited in claim 19, wherein the coupling member includes a break off portion and further comprising the step of engaging the coupling member with the surgical driver.

\* \* \* \* \*